(12) United States Patent
Mukkamala

(10) Patent No.: US 6,734,149 B2
(45) Date of Patent: *May 11, 2004

(54) COMBINATION OF ADDITIVES FOR LUBRICATING OILS

(75) Inventor: Ravindranath Mukkamala, Houston, TX (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/166,413

(22) Filed: Jun. 10, 2002

(65) Prior Publication Data

US 2002/0198115 A1 Dec. 26, 2002

Related U.S. Application Data

(63) Continuation-in-part of application No. 10/054,058, filed on Jan. 22, 2002.
(60) Provisional application No. 60/263,776, filed on Jan. 24, 2001.

(51) Int. Cl.[7] ................. C10M 141/00; C07D 233/30
(52) U.S. Cl. ................. 508/284; 508/285; 508/286; 508/375; 548/316.4
(58) Field of Search .......................... 508/284

(56) References Cited

U.S. PATENT DOCUMENTS

| | | |
|---|---|---|
| 4,188,297 A | 2/1980 | Jayne et al. |
| 4,189,587 A | 2/1980 | Holt et al. .................. 548/312 |
| 4,589,991 A | 5/1986 | Ryer et al. |
| 4,661,273 A | 4/1987 | Frangatos et al. |
| 4,917,809 A | 4/1990 | Zinke et al. |
| 5,057,612 A | 10/1991 | Worley et al. |
| 5,318,712 A | 6/1994 | Lange et al. |
| 5,597,785 A | 1/1997 | Karol |
| 6,187,722 B1 | 2/2001 | Rowland et al. |
| 6,602,831 B2 * | 8/2003 | Mukkamala ................. 508/284 |
| 6,602,832 B2 * | 8/2003 | Mukkamala et al. ....... 508/284 |

FOREIGN PATENT DOCUMENTS

| | | |
|---|---|---|
| EP | 0380814 B1 | 8/1994 |
| EP | 0728747 A1 | 8/1996 |
| GB | 1053716 | 1/1967 |
| WO | WO 01/62739 A2 | 8/2001 |

OTHER PUBLICATIONS

Smalheer et al, "Lubricant Additives", Section I—Chemistry of Additives, pp. 1–11, 1967.*
John D. Christian; Imidazolidinethiones; J. Org. Chem. vol. 22; pp. 396–399 (1957).
Martino Paventi et al.; Canadian Journal of Chemistry; vol. 65; pp. 282–289 (1987).
Te–Chen Tsao et al.; Novel N–Halamine Disinfectant Compounds; Biotechnol. Prog., vol. 7,; pp. 60–66 (1991).
A E. Oberster, et al.; New Nondiscoloring Stabilizer System For SBR and Stereospecific Diene Polymers; Rubber Chemistry and Technology; pp. 255–270; (1968).
D.F. Bushey et al.; Syntheses and Stereochemistry of Amidoximes, J. Org. Chem, 45 (21) pp. 4198–4206 (1980).
M.D. Nair et al.; Dispiroimidazolidinethiones, Indian J. Org. Chem, 5 pp. 290–293 (1967).
W. J. Middleton et al.; Fluorinated Aminoimidazolines. Synthesis and Determination of Tautomeric Structure, J. Org. Chem, 35 (5) pp.1480–1485 (1970).
F. Asinger et al.; Zum Substitutionsverhalten von Imidazolidin–4–thionen, Monatshefte fur chemie 107 pp. 35–41 (1976) (in German).
M. A. Voinov et al.; Reactions of Aldonitrones (3–Imidazolines–3–oxide Derivatives) with isothiocyanates 11, pp. 2642–2647 (1992) (in Russian).

* cited by examiner

Primary Examiner—Ellen M McAvoy
(74) Attorney, Agent, or Firm—Kenneth Crimaldi

(57) ABSTRACT

A composition comprising a compound of formula I:

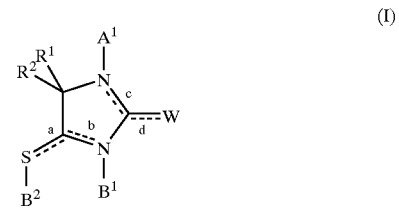

wherein W represents O, S—$A^2$, or two groups, $R^3$ and $R^4$; bonds a and b are single or double bonds, provided that one of a and b is a single bond and the other is a double bond; c is a single or double bond, and d is a single bond, double bond, or two single bonds, provided that d is a single bond when c is a double bond, d is not a single bond when c is a single bond, and W is $R^3$ and $R^4$ when d is two single bonds; $A^1$, $A^2$, $B^1$ and $B^2$ are independently hydrogen, alkyl, alkenyl, aralkyl or one of the groups depicted in Scheme 1:

Scheme 1

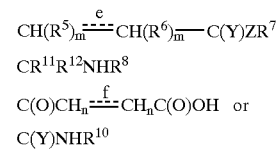

and a dithiophosphate.

16 Claims, No Drawings

COMBINATION OF ADDITIVES FOR LUBRICATING OILS

CROSS REFERENCE TO RELATED PATENT APPLICATIONS

This is a continuation-in-part of co-pending application Ser. No. 10/054,058, filed Jan. 22, 2002, which claims priority from provisional application serial No. 60/263,776, filed Jan. 24, 2001.

BACKGROUND

This invention relates generally to combinations of oil-soluble additives for lubricating oils.

Zinc dialkyldithiophosphates (ZDDP) are widely used as lubricant additives. The principal disadvantages of these compounds are that an ash residue is produced by the zinc as the additive is consumed, and that phosphorus is known to affect the efficiency of catalytic converters in motor vehicles, thereby causing emissions problems. Dithiohydantoin compounds are disclosed in European Patent Application No. EP 0 728 747 A1. However, the compounds are not within the scope of the present invention, and moreover, are disclosed only for pharmaceutical applications.

The problem addressed by this invention is to find improved oil-soluble additives for lubricating oils.

STATEMENT OF INVENTION

The present invention is directed to a composition comprising:
(a) from 1% to 99% of at least one compound of formula I:

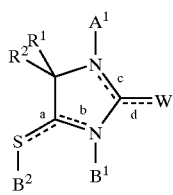

wherein W represents O, S—$A^2$, or two groups, $R^3$ and $R^4$; bonds a and b are single or double bonds, provided that one of a and b is a single bond and the other is a double bond; c is a single or double bond, and d is a single bond, double bond, or two single bonds, provided that d is a single bond when c is a double bond, d is not a single bond when c is a single bond, and W is $R^3$ and $R^4$ when d is two single bonds;

$A^1$, $A^2$, $B^1$ and $B^2$ are independently hydrogen, alkyl, alkenyl, aralkyl or one of the groups depicted in Scheme 1:

Scheme 1

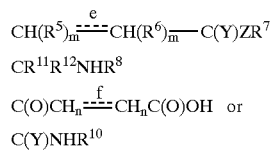

provided that $B^1$ is absent when b is a double bond, $B^2$ is absent when a is a double bond, $A^1$ is absent when c is a double bond and $A^2$ is absent when d is a double bond; and provided that $A^2$ or $B^2$ is not aralkyl when W is O or S—$A^2$;

$R^1$, $R^2$, $R^3$ and $R^4$ are independently hydrogen, alkyl, alkenyl, aryl or aralkyl; or $R^1$ and $R^2$, or $R^3$ and $R^4$, combine with the carbon atom to which they are attached to form an alkyl or alkenyl ring; Y is O or S; Z is O, S or $NR^9$; m is 0 when bond e is a double bond and 1 when e is a single bond; n is 1 when bond f is a double bond and 2 when f is a single bond; $R^5$ is $C(Y)ZR^7$, hydrogen or $C_1$–$C_4$ alkyl; $R^6$ is hydrogen or $C_1$–$C_4$ alkyl; $R^7$, $R^8$, $R^9$, $R^{10}$, $R^{11}$ and $R^{12}$ are independently hydrogen, alkyl, alkenyl, aryl or aralkyl;

provided that at least one of $A^1$, $A^2$, $B^1$ and $B^2$ is present and is not hydrogen; and (b) from 1% to 99% of at least one dithiophosphate.

The present invention is further directed to a composition comprising a lubricating oil, from 0.05% to 15% of a compound of formula I, and from 0.01% to 10% of a dithiophosphate; and to a method for improving the anti-wear and anti-corrosion characteristics of a lubricating oil by adding from 0.05% to 15% of a compound of formula I, and from 0.01% to 10% of a dithiophosphate.

DETAILED DESCRIPTION

All percentages are weight percentages based on the entire composition described, unless specified otherwise. An "alkyl" group is a saturated hydrocarbyl group having from one to twenty-two carbon atoms in a linear, branched or cyclic arrangement, and having from 0 to 2 oxygen, nitrogen or sulfur atoms. Substitution on alkyl groups of one or more halo, hydroxy, alkoxy, alkanoyl or amido groups is permitted; alkoxy, alkanoyl and amido groups may in turn be substituted by one or more halo substituents. In one preferred embodiment, alkyl groups contain from one to twelve carbon atoms and from 0 to 1 oxygen, nitrogen or sulfur atoms; in another preferred embodiment, alkyl groups contain from 12 to 22 carbon atoms, and more preferably, no heteroatoms. An "alkenyl" group is an "alkyl" group in which at least one single bond has been replaced with a double bond. An "alkanoyl" group is an alkyl group linked through a carbonyl group, e.g., an acetyl group. An "aryl" group is a substituent derived from an aromatic compound, including heterocyclic aromatic compounds having heteroatoms chosen from among nitrogen, oxygen and sulfur. An aryl group has a total of from five to twenty ring atoms, and has one or more rings which are separate or fused. Substitution on aryl groups of one or more halo, alkyl, alkenyl, hydroxy, alkoxy, alkanoyl or amido groups is permitted, with substitution by one or more halo groups being possible on alkyl, alkenyl, alkoxy, alkanoyl or amido groups. An "aralkyl" group is an "alkyl" group substituted by an "aryl" group. A "lubricating oil" is a natural or synthetic oil, or a mixture thereof, having suitable viscosity for use as a lubricant, e.g., as crankcase oil in an internal combustion engine, automatic transmission fluid, turbine lubricant, gear lubricant, compressor lubricant, metal-working lubricant, hydraulic fluid, etc.

A "dithiophosphate" is any compound having a dithiophosphate group, preferably a dithiophosphate ester group {$(RO)_2P(S)S$—, where the R groups are the same or different alkyl, aryl, aralkyl or alkenyl groups}, for example, a dialkyldithiophosphate group, a diaralkyldithiophosphate group, or a combination thereof. Examples of dialkyldithiophosphates include, but are not limited to, S-alkanoyl dialkyldithiophosphates, S-alkyl dialkyldithiophosphates and ZDDP. The term "ZDDP" refers to a zinc dialkyldithiophosphate having the structure

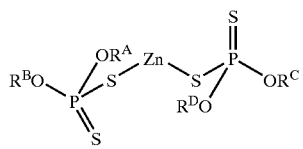

wherein $R^A$, $R^B$, $R^C$ and $R^D$ independently represent $C_1$–$C_{22}$ alkyl groups. Preferably, alkyl groups are primary or secondary alkyl groups. Preferably, alkyl groups are $C_2$–$C_{12}$ alkyl groups, more preferably $C_2$–$C_8$ alkyl groups, and most preferably $C_3$–$C_6$ alkyl groups.

In formula I and Scheme 1, the letter a, b, c, d, e or f represents the total bonding between the atoms adjacent to each letter, e.g., when "a" represents a single bond, the sulfur atom and ring carbon to which it is attached are connected by a single bond. These letters are used in formula I to indicate that the compound may exist in different tautomeric forms, e.g., when the sulfur shown in formula I is substituted, i.e., $B^2$ is present, a is a single bond, b is a double bond and $B^1$ is absent, as will be understood by one skilled in the art. In the substituent groups of Scheme 1, e and f indicate whether the bond between the adjacent carbons is a single or double bond, which is determined by the alkylating agent used to introduce the substituent, as described hereinbelow.

It is preferred that at least one of $A^1$, $A^2$, $B^1$ and $B^2$ is present and is not hydrogen or methyl. It is preferred that if the only one of $A^1$, $A^2$, $B^1$ and $B^2$ which is present, and is not hydrogen, is alkyl, then it is $C_8$–$C_{22}$ alkyl, more preferably $C_{16}$–$C_{22}$ alkyl, i.e., it is preferred that any alkyl group attached to nitrogen or sulfur is in one of the aforementioned ranges. It is also preferred that $A^1$, $A^2$, $B^1$ and $B^2$ are independently hydrogen or one of the three groups depicted in Scheme 1. It is also preferred that W is $R^3$ and $R^4$, and c is a single bond. It is also preferred that W is $R^3$ and $R^4$, c is a single bond, $A^1$ is hydrogen, and $B^1$ or $B^2$ is one of the groups depicted in Scheme 1.

Preferably, Y and Z are O, e is a single bond, m is one and $R^5$ and $R^6$ independently are hydrogen or methyl. Preferably, $R^7$ is alkyl. In one aspect of the invention, a tetraalkylimidazolidinethione (TAIT), or an imidazolidinethione having from one to three alkyl groups, is alkylated with an acrylate ester to produce a compound having a —CHR$^5$CHR$^6$C(O)OR$^7$ group, as shown below for an alkyl acrylate, resulting in $R^5$=$R^6$=H and $R^7$=alkyl. Reaction with methacrylate or crotonate esters, resulting in $R^6$=CH$_3$ or $R^5$=CH$_3$, respectively, also is possible. If $R^1$, $R^2$, $R^3$ and $R^4$ are all methyl, the TAIT is known as TMIT.

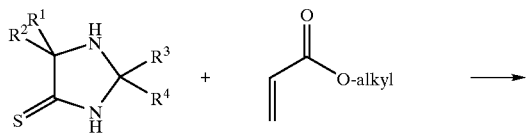

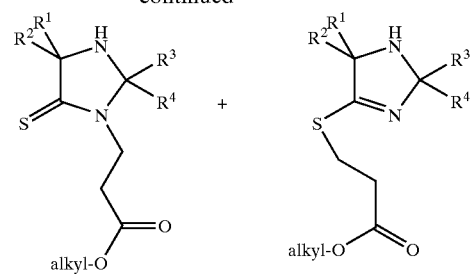

The extent of N-alkylation versus S-alkylation varies with the identity of the R groups on the imidazolidenethione ring and with the alkylating agent, as shown below in the Examples.

In another aspect of this invention, a TAIT or an imidazolidinethione having from one to three alkyl groups is alkylated with an alkyl propiolate to produce a compound in which the ester side chain has a carbon—carbon double bond. In another aspect of this invention, a TAIT or an imidazolidinethione having from one to three alkyl groups is alkylated with an imine, CR$^{11}$R$^{12}$=NR$^8$. Preferably, R$^8$ is $C_{12}$–$C_{22}$ alkyl. Preferably, R$^{11}$ and R$^{12}$ independently are alkyl or hydrogen. In a preferred embodiment of the invention, CR$^{11}$R$^{12}$=NR$^8$ is a formaldehyde imine, CH$_2$=NR$^8$. In another aspect of this invention, a TAIT or an imidazolidinethione having from one to three alkyl groups is alkylated with maleic or succinic anhydride to produce a compound having a —C(O)CH=CHC(O)OH or —C(O)CH$_2$CH$_2$C(O)H side chain, respectively, with alkylation occurring mainly on the sulfur. In another aspect of this invention, a TAIT or an imidazolidinethione having from one to three alkyl groups reacts with an isocyanate or isothiocyanate to produce a compound having a —C(O)NHR$^{10}$ or —C(S)NHR$^{10}$ group, respectively. Preferably, R$^{10}$ is aryl, alkyl or aralkyl, more preferably aryl or $C_8$–$C_{20}$ alkyl.

In one embodiment of the invention, the group ZR$^7$ in a —CHR$^5$CHR$^6$C(Y)ZR$^7$ side chain or a —CH=CHC(Y)ZR$^7$ side chain contains a thioethyl group, i.e., a group having the structure —CH$_2$CH$_2$S—, where one of the CH$_2$ and the sulfur is attached to the C(Y) functionality and the other is attached to an alkyl, alkenyl or aralkyl group. For example, ZR$^7$ can be OCH$_2$CH$_2$S—R, where R is alkyl, alkenyl or aralkyl; when Y is O, and R$^5$ and R$^6$ are H, the side chain is —CH$_2$CH$_2$C(O)OCH$_2$CH$_2$S—R.

In one embodiment of the invention, $A^1$, $A^2$, $B^1$ and $B^2$ are independently hydrogen or one of the groups depicted in Scheme 2:

Scheme 2

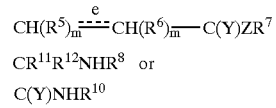

CR$^{11}$R$^{12}$NHR$^8$ or

C(Y)NHR$^{10}$

Preferably, Y and Z are O, e is a single bond, m is 1, and R$^5$ and R$^6$ independently are hydrogen or methyl. Preferably, R$^8$ is $C_{12}$–$C_{22}$ alkyl. Preferably, $A^1$, $A^2$, $B^1$ and $B^2$ are independently hydrogen or one of the groups depicted in Scheme 3:

Scheme 3

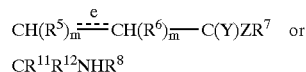

Preferably, a synergistic combination of lubricant additives comprises from 10% to 90% of a compound of formula I and from 10% to 90% of a dithiophosphate, more preferably from 20% to 80% of a compound of formula I and from 20% to 80% of a dithiophosphate, more preferably from 25% to 75% of a compound of formula I and from 25% to 75% of a dithiophosphate, and most preferably from 40% to 60% of a compound of formula I and from 40% to 60% of a dithiophosphate. In one embodiment, the synergistic combination contains less than 10% of any other ingredient, more preferably less than 5%, more preferably less than 1%, and most preferably is substantially free of other ingredients. In another embodiment of the invention, other additives typically used in lubricating oils are present in the composition. Such additives include, but are not limited to, dispersants, detergents, antioxidants, antifoamants, friction modifiers, seal swell agents, demulsifiers, viscosity index improvers and pour point depressants. In a preferred embodiment of the invention, from 0.05% to 10% each of a compound of formula I and a dithiophosphate are added to a lubricating oil, more preferably, from 0.1% to 5% each, more preferably, from 0.1% to 2% each, more preferably, from 0.2% to 2% each, more preferably from 0.2% to 1% each, and most preferably, from 0.2% to 0.6% each. Preferably, the ratio of the amount of the compound of formula I to the amount of a dithiophosphate is from 1:9 to 9:1, more preferably from 1:4 to 4:1, more preferably from 1:3 to 3:1, and most preferably from 2:3 to 3:2. Preferably, the dithiophosphate is a dialkyldithiophosphate, most preferably a ZDDP. A lubricating oil is a natural or synthetic oil, having suitable viscosity for use as a lubricant, or a mixture thereof.

EXAMPLES

Example 1

Alkylation of Tetraalkylimidazolidinethiones with Alkyl Acrylates

TMIT was prepared according to the procedure given in U.S. Pat. No. 5,057,612, as follows.

To a mechanically-stirred mixture of ammonium sulfide (0.4 moles, 136 mL, 20 wt % aqueous solution), sodium cyanide (14.7 g, 0.3 moles), ammonium chloride (16.1 g, 0.3 moles) and water (80 mL), acetone (44 mL, 0.6 moles) was added drop-wise over a period of 30 min.; during the addition of acetone, the reaction temperature rose to about 36° C. The reaction mixture was then externally heated to 65° C. for a period of 6–7 hours. The reaction mixture was cooled to 0–5° C. using an ice bath, and the white solid was filtered, washed with cold water and suction dried. The yield of TMIT was 44.6 grams (94%); melting point: 155° C. IR: 3521, 2976, 1657, 1524, 1462 cm$^{-1}$; $^1$H NMR (CDCl$_3$, 500 MHz): δ 1.46 (s, 6 H), 1.44 (s, 6 H) ppm; $^{13}$C NMR (CDCl$_3$, 125 MHz): δ 207.7, 78.4, 70.9, 29.9, 29.9 ppm.

7,14-diazadispiro[5.1.5.2]pentadecane-15-thione (DDPT),

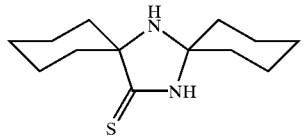

was prepared according to the procedure described for TMIT from ammonium sulfide (0.4 moles, 136 mL, 20 wt % aqueous solution), sodium cyanide (14.7 g, 0.3 moles), ammonium chloride (16.1 g, 0.3 moles) and water (80 mL); with addition of cyclohexanone (58.8 g, 0.6 moles). The product was obtained as a white solid (69.8 grams, 98%), and melted at 229° C. IR: 3127, 2925, 2855, 1516, 1454 cm$^{-1}$; $^1$H NMR (CDCl$_3$, 500 MHz): δ 9.8 (bs, 1H), 1.9(dt, 2H), 1.8–1.2 (m, 18H) ppm; $^{13}$C NMR (CDCl$_3$, 125 MHz): δ 207.8, 81.0, 72.9, 39.6, 37.8, 24.9, 24.6, 23.0, 21.9 ppm.

Unless otherwise specified, tetraalkylimidazolidinethiones were allowed to react with alkyl acrylates in acetonitrile in the presence of 50 mole % of Cs$_2$CO$_3$ at room temperature for 10–15 hours (TMIT) or for 5 hours (DDPT) to produce compounds having the following structure:

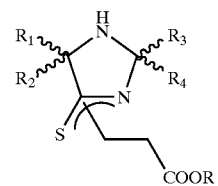

Detailed procedures and product analyses for several products are presented in Examples 2–8. The acrylates are abbreviated as follows: MA=methyl acrylate; 2-EHA=2-ethylhexyl acrylate; LA=lauryl acrylate; BA=butyl acrylate; and TUA=3-thiaundecyl acrylate. Yield is given in %, the ratio of N-alkylated adduct to S-alkylated adduct (N/S) as a ratio of percentages or as "nd" (not determined), the physical state (state) as "L" (liquid), "SS" (soft solid) or "SG" (sticky gum), and the oil solubility (oil sol) as a weight percent. Oil solubility was measured at room temperature in EXCEL HC 100 lubricating base oil (available from Pennzoil Corp.). The adduct ratio, N/S, was determined from integration of proton NMR signals. The results for all acrylate adducts are presented below in Table 1.

Example 2

Adduct of TMIT and 2-EHA

A mixture of TMIT (1.0 g, 6.33 mmol), 2-ethylhexyl acrylate (1.16 g, 6.33 mmol) and cesium carbonate (1.0 g, 3.3 mmol) in acetonitrile (15 mL) was stirred at room temperature for 24 h. The reaction mixture was filtered to separate solid cesium carbonate and solvent was evaporated from the filtrate to obtain the product as a colorless oil (1.9 g, 88%). IR: 3325, 2961, 1732, 1595, 1480 cm$^{-1}$; $^1$H NMR (CDCl$_3$, 500 MHz): δ 3.96 (overlapping d, 2 H), 3.83 (t, 1.72 H), 3.22 (t, 0.28 H), 2.82 (t, 1.72 H), 2.71 (t, 0.28 H), 1.91 (bs, 1H), 1.42 (s, 6 H), 1.40 (s, 6H), 1.35–1.20 (m, 8 H), 0.85 (overlapping t, 6 H) ppm; $^{13}$C NMR (CDCl$_3$, 125 MHz): δ 205.8, 173.6, 171.9, 171.3, 130.2, 128.5, 88.7, 82.9, 70.35, 69.6, 67.2, 66.9, 66.8, 40.6, 38.6, 33.9, 31.4, 30.26, 30.21, 28.79, 28.71, 28.23, 25.8, 23.64, 22.83, 13.9, 10.9 ppm.

Example 3

Adduct of TMIT and LA

A procedure similar to that of Example 2 was used. Starting from TMIT (1.0 g, 6.33 mmol), lauryl acrylate (1.5 g, 6.33 mmol) and cesium carbonate (1.0 g, 3.3 mmol) in acetonitrile (15 mL), the product was isolated as a colorless oil (1.7 g, 68%). IR: 3326, 2925, 1732 1596, 1480 cm$^{-1}$; $^1$H NMR (CDCl$_3$, 500 MHz): δ 4.18 (overlapping d, 2H), 3.86 (t, 1.78 H), 3.36 (t, 0.22 H), 2.85 (t, 1.78 H), 2.75 (t, 0.22 H), 1.90 (bs, 1H), 1.62 (m, 2H), 1.48 (s, 6H), 1.44 (s, 6H), 1.4–1.2 (m, 18H), 0.88 (t, 3H) ppm.

Example 4

Adduct of TMIT and BA

A procedure similar to that of Example 2 was used. Starting from TMIT (1.0 g, 6.33 mmol), n-butyl acrylate (0.81 g, 6.33 mmol) and cesium carbonate (1.0 g, 3.3 mmol) in acetonitrile (15 mL), the product was isolated as a colorless oil (1.3 g, 72%). IR: 3323, 2961, 1732, 1582, 1483 cm$^{-1}$; $^1$H NMR (CDCl$_3$, 500 MHz): δ 4.08 (t, 2H), 3.85 (t, 2H), 2.84 (t, 2H), 1.95 (bs, 1 H), 1.60 (m, 2H), 1.46 (s, 6H), 1.42 (s, 6H), 1.36 (m, 2H), 0.91 (t, 3H) ppm.

Example 5

Adduct of DDPT and LA

A procedure similar to that of Example 2 was used. Starting from DDPT (1.0 g, 4.2 mmol), lauryl acrylate (1.0 g, 4.2 mmol) and cesium carbonate (0.68 g, 2.1 mmol) in acetonitrile (25 mL), the product was isolated as a light-yellow, low-melting solid (1.9 g, 95%). IR: 2927, 2845, 1733, 1474 cm$^{-1}$; $^1$H NMR (CDCl$_3$, 500 MHz): δ 4.15 (t, 2H), 3.85 (t, 2H), 2.85 (t, 2H), 2.03 (dt, 2H), 1.8–1.2 (m, 38 H), 0.88 (t, 3H) ppm.

Example 6

Adduct of TAIT Mixture Prepared from Acetone/Methyl Isobutyl Ketone/Methyl Ethyl Ketone/Cyclohexanone and EHA A TAIT mixture was prepared from an equimolar mixture of the four title ketones according to the procedure used for preparation of TMIT, using ammonium sulfide (136 mL, 0.4 moles, 20 wt % aqueous solution), sodium cyanide (14.7 g, 0.3 moles), ammonium chloride (16.1 g, 0.3 moles), water (80 mL), cyclohexanone (14.7 g, 0.15 moles), acetone (8.7 g, 0.15 moles) ethyl methyl ketone (10.8 g, 0.15 moles), and methyl isobutyl ketone (15.0 g, 0.15 moles) to obtain an oily layer at the end of the heating period. The oil layer was extracted into chloroform (350 mL), washed with water and dried with anhydrous potassium carbonate. Solvent evaporation yielded the product as a thick oil that slowly turned into a sticky gray solid (36 grams, yield: 55% for an average molecular weight of 220). IR: 3361, 2962, 2874, 1605, 1520, 1459 cm$^{-1}$; $^1$H NMR (CDCl$_3$, 500 MHz): δ 2.24 (d), 2.06 (s), 1.85–1.91 (m), 1.86–1.56 (m), 1.50–1.46 (m), 1.45–1.34 (m), 1.26–1.11 (bm), 1.39 (t), 0.99 (dd), 0.95–0.84 (m) ppm; $^{13}$C NMR (CDCl$_3$, 125 MHz): δ 207.8, 207.62, 207.60, 207.43, 207.40, 207.01, 206.89, 206.68, 206.66, 81.6, 81.18, 81.14, 80.70, 80.65, 78.38, 78.31, 73.95, 73.30, 72.82, 70.79, 70.46, 70.18 and several peaks between 40–10 ppm.

A procedure similar to that of Example 2 was used for the reaction with 2-EHA. Starting from the TAIT product described in the preceding paragraph (1.0 g, ca. 4.5 mmol), 2-ethylhexyl acrylate (0.82 g, 4.5 mmol) and cesium carbonate (0.75 g, 2.25 mmol) in acetonitrile (20 mL), the product was isolated as a yellow oil and solid mixture (1.8 g, 99%). IR: 3325, 2933, 2860, 1732, 1480 cm$^{-1}$.

Example 7

Adduct of TAIT Mixture Prepared from Methyl Ethyl Ketone and BA

A cis-trans TAIT mixture was obtained by applying the procedure used for preparation of TMIT to ammonium sulfide (136 mL, 0.4 moles, 20 wt % aqueous solution), sodium cyanide (14.7 g, 0.3 moles), ammonium chloride (16.1 g, 0.3 moles), water (80 mL), and ethyl methyl ketone (54.1 g, 0.75 moles) to obtain an oily layer at the end of the heating period. The oil layer was extracted into chloroform (350 mL), washed with water and dried with anhydrous potassium carbonate. Solvent evaporation yielded the product as a thick oil that turned into a sticky dirty-white solid. This solid was washed quickly with cold water and suction dried to give a white powder (23 g, yield: 41%) that melted at 72° C. IR: 3320, 3128, 2966, 1533, 1457, 1371 cm$^{-1}$; $^1$H NMR (CDCl$_3$, 500 MHz): δ 1.85–1.65 (m, 4H), 1.44–1.36 (4s, 6H), 0.99–0.91 (m, 6H) ppm; $^{13}$C NMR (CDCl$_3$, 125 MHz): δ 207.15, 207.07, 81.24, 81.17, 73.69, 73.51, 35.49, 34.99, 33.85, 33.56, 28.56, 28.29, 27.82, 27.24, 8.55, 8.46, 8.25 ppm.

A procedure similar to that of Example 2 was used for the reaction with BA. Starting from the TAIT product described in the preceding paragraph (4.0 g, 21.5 mmol), n-butyl acrylate (2.8 g, 21.5 mmol) and cesium carbonate (3.5 g, 10.8 mmol) in acetonitrile (50 mL), the product was isolated as a yellow oil (6.1 g, 90%). IR: 3351, 2965, 2875, 1732, 1482 cm$^{-1}$; $^1$H NMR (CDCl$_3$, 500 MHz): δ 4.05 (t, 2H), 3.95 (m), 3.80 (m), 3.63 (m), 2.95 (m), 2.82 (m), 2.67 (m), 1.80–1.51 (m, 6 H), 1.35 (m, 8H), 0.88 (m, 9H) ppm; $^{13}$C NMR (CDCl$_3$, 125 MHz): δ 205.31, 205.05, 171.2, 85.77, 85.67, 72.44, 72.21, 64.48, 40.28, 34.55, 33.93, 32.65, 33.63, 31.06, 31.03, 30.38, 28.61, 28.21, 26.46, 26.33, 18.91, 13.49 ppm.

Example 8

Adduct of TMIT and 3-Thiaundecyl Acrylate

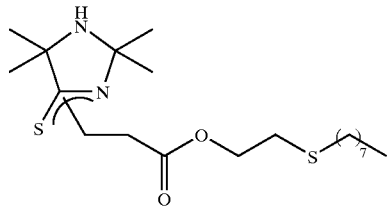

A procedure similar to that of Example 2 was used. Starting from TMIT (1.0 g, 6.33 mmol), 3-thiaundecyl acrylate (1.4 g, 6.33 mmol) and cesium carbonate (1.0 g, 3.3 mmol) in acetonitrile (20 mL), the product was isolated as a light yellow oil (2.0 g, 83%). IR: 2961, 1734, 1481 cm$^{-1}$; $^1$H NMR (CDCl$_3$, 500 MHz): δ 4.22 (t, 2H), 3.84 (t, 2H), 2.84 (t, 2H), 2.71 (t, 2H), 2.52 (t, 2H), 1.55 (m, 2H), 1.46 (s, 6H), 1.42 (s, 6H), 1.4–1.2 (m, 10H), 0.85 (t, 3H) ppm; $^{13}$C NMR (CDCl$_3$, 125 MHz): δ 205.9, 170.9, 82.9, 69.5, 63.7, 40.4, 32.2, 31.6, 31.3, 30.2, 30.1, 29.5, 29.0, 28.6, 28.2, 22.4, 13.9 ppm.

TABLE 1

TAIT-Acrylate Ester Addition Products and Oil Solubilities

| Ex. No. | TAIT | acrylate | yield | N/S | state | oil sol |
|---|---|---|---|---|---|---|
| | TMIT | MA | 85 | 83/17 | L | <2 |
| 2 | TMIT | 2-EHA | 88 | 86/14 | L | >20[a] |
| 3 | TMIT | LA | 68 | 89/11 | L | >20[a] |
| 4 | TMIT | BA | 72 | >97/<3 | L | <5 |
| | DDPT | MA | 20 | >99/<1 | SS | <5 |
| | DDPT | BA | 96 | >99/<1 | SS | <5 |
| | DDPT | 2-EHA | 95 | >99/<1 | SG | ca. 5[b] |
| 5 | DDPT | LA | 95 | ca. 95/5 | SG | ca. 10[b] |
| | mixture[c] | 2-EHA | 89 | nd | L | ca. 10 |
| 6 | mixture[d] | 2-EHA | 99 | nd | L | ca. 10 |
| | mixture[d] | LA | 99 | nd | L/S | ca. 10 |
| 7 | mixture[e] | BA | 90 | nd | L | >10 |
| 8 | TMIT | TUA | 83 | >95/<5 | L | ca. 5 |

[a]Miscible at room temperature to give a single clear phase.
[b]The mixture with oil was an unclear dispersion, with the product from lauryl acrylate being more clear than that from 2-ethylhexyl acrylate.
[c]TAIT produced from equimolar mixture of acetone/methyl isobutyl ketone/cyclohexanone.
[d]TAIT produced from equimolar mixture of acetone/methyl isobutyl ketone/methyl ethyl ketone/cyclohexanone.
[e]TAIT cis/trans mixture produced from methyl ethyl ketone.

Example 9

Efficacy Testing and Performance

Efficacy of four oil formulations was tested, including a base oil and one containing a commercial anti-wear ZDDP-based additive, ELCO-103. The samples tested were as follows: (1) EXCEL HC 100 base oil (available from Pennzoil Products Co., West Lake, La.); (2) EXCEL HC 100 with 1% ELCO 103; (3) EXCEL HC 100 with 1% of the adduct of 2-EHA and TMIT (see Example 2); and (4) EXCEL HC 100 with 1% of an imine adduct of TMIT (see Example 15). Details of the tests are as follows:

4-Ball anti-wear test (ASTM D-4172). Load: 40 Kg; Temp: 75° C.; Rotation rate: 1200 rpm; Time: 1 hour; Measured parameter: wear scar diameter in mm on the steel balls. The smaller the scar diameter, the more effective a given anti-wear additive.

Load carrying capacity (EP test, ASTM D-2783). Similar to the anti-wear test above, but starts at room temperature and the load on four rotating balls is constantly increased until the balls weld to each other. The quantities measured to assess performance are weld point load (kgf), scar diameter (mm at 100 kgf or 126 kgf) just before weld point, and load wear index (LWI) (average of sum of the corrected loads determined for 10 applied loads preceding the weld point, kgf). A higher LWI is an indication of better anti-wear properties.

Copper corrosion test (ASTM D-130). Copper metal specimens are immersed in the oil sample at 212° F. (100° C.) for three hours, and the appearance is then rated based on the tarnish acquired. Here, a lower rating reflects lesser corrosivity. For example, a rating of "1" indicates only a slight tarnish, with "1A" being a light orange and "1B" a dark orange; "2" would indicate moderate tarnish, with ratings of "A" through "E" indicating progressively darker colors.

Results of the tests are presented below in Table 2.

TABLE 2

Test Results for Lubricating Oils

| | ASTM D-4172 | ASTM D-130 | EP Test | |
|---|---|---|---|---|
| sample | scar diameter | corrosion | scar diameter[b] | LWI |
| 1 | 0.84 | 1B[a] | 2.99 @ 100 | 10.8 |
| 2 | 0.64 | 1A[a] | 2.1 @ 100 | 21.5 |
| 3 | 0.63 | 1A[a] | 2.45 @ 100 | 14.5 |
| 4 | 0.65 | 1A[a] | 2.47 @ 126 | 18.8 |

[a]Each sample had a slight tarnish.
[b]The actual weld point of samples 1–3 was 126 kgf, and that of sample 4 was 160 kgf.

Example 10

Adduct of TMIT and Methyl Iodide

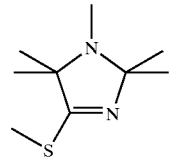

A mixture of TMIT (2.0 g, 12.6 mmol), methyl iodide (5.6 g, 40 mmol), and anhydrous potassium carbonate (8.3 g, 138.2 mmol) in chloroform (45 mL) were stirred at room temperature for 2 days. The mixture was filtered, and solvent was evaporated to obtain the product depicted above as a liquid (1.9 g, 83%). $^1$H NMR (CDCl$_3$, 500 MHz): δ 2.38 (s, 3H), 2.26 (s, 3H), 1.25 (s, 6H), 1.16 (s, 6H) ppm; $^{13}$C NMR (CDCl$_3$, 125 MHz): δ 175.1, 88.9, 70.3, 27.5, 26.4, 24.6, 12.6 ppm. The product was soluble in EXCEL HC 100 lubricating base oil only in an amount below 1% by weight.

Example 11

Adduct of DDPT and Methyl Iodide

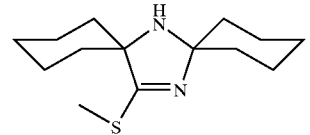

A mixture of DDPT (3.0 g, 12.6 mmol), methyl iodide (5.6 g, 40 mmol), and anhydrous potassium carbonate (8.3 g, 138.2 mmol) in chloroform (30 mL) was stirred at room temperature for 2 days. The mixture was filtered, and solvent was evaporated to obtain the product as a thick liquid (2.45 g, 77%) that slowly turned into a soft solid. $^1$H NMR (CDCl$_3$, 500 MHz): δ 2.41 (s, 3H), 1.75–1.1 (m, 20 H) ppm; $^{13}$C NMR (CDCl$_3$, 125 MHz): δ 174.9, 90.5, 72.6, 40.3, 37.5, 25.4, 25.2, 23.4, 22.4, 13.5 ppm. The product was soluble in EXCEL HC 100 at 5 weight % at room temperature, and remained clear at room temperature after 1 week.

Example 12

Adduct of TMIT and Methyl Propiolate

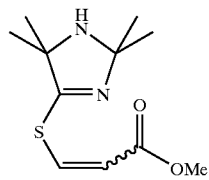

A mixture of TMIT (1.0 g, 6.33 mmol) and methyl propiolate (0.53 g, 6.33 mmol) in chloroform (15 mL) was stirred at room temperature for 24 h, followed by heating at 45° C. for another 24 h. Solvent evaporation yielded the product depicted above as a light-yellow, crystalline solid (1.4 g, 92%). IR: 3329, 2974, 1706, 1606, 1436 cm$^{-1}$; $^1$H NMR (CDCl$_3$, 500 MHz): δ 8.29 (d, J=16.0 Hz, 0.12 H), 8.15 (d, J=10 Hz, 0.88 H), 6.16 (d, J=16 Hz, 0.12 H), 6.19 (d, J=10 Hz, 0.88 H), 3.7 (s, 3H), 1.47 (s, 0.72 H), 1.45 (s, 0.72 H), 1.42 (s, 5.3 H), 1.36 (s, 5.3 H) ppm; $^{13}$C NMR (CDCl$_3$, 125 MHz): δ 171.4, 169.6, 166.9, 141.3, 140.6, 118.9, 115.5, 114.1, 51.6, 30.5, 30.07, 30.06, 28.3 ppm. The product is an 85/15 mixture of cis/trans isomers. The product was soluble in EXCEL HC 100 at 10 weight % at 100° C., but precipitated at room temperature after 30 minutes.

Example 13

Adduct of Example 12 Product with Methyl Propiolate

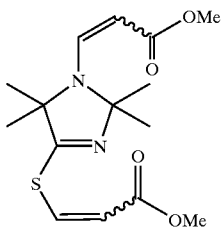

A mixture of the product made in Example 12 (0.1 g, 0.6 mmol) and methyl propiolate (0.053 g, 0.6 mmol) in deuterated chloroform (CDCl$_3$, 1 mL) was left at room temperature 3 days and then heated for 40 h at 45° C. Solvent evaporation yielded RM-297 as a light-yellow, crystalline solid (1.5 g, 99%). IR: 2974, 1701, 1683, 1617, 1602, 1454 cm$^{-1}$; $^1$H NMR (CDCl$_3$, 500 MHz): δ 8.29 (d, J=16.0 Hz), 8.08 (d, J=10 Hz), 8.075 (d, J=10 Hz), 7.36 (d, J=15 Hz), 6.09 (d, J=16 Hz), 6.08 (d, J=10 Hz), 6.03 (d, J=10 Hz), 4.73 (d, J=15 Hz), 3.71–3.69 (4 s, —CH$_3$), 1.48, 1.44, 1.34, 1.29 (4 s, —CH$_3$) ppm. The cis/trans ratio in the side chain attached to sulfur is 85/15, and in that attached to nitrogen it is 5/95. The product was soluble in EXCEL HC 100 at less than 5 weight % at 100° C.

Example 14

Adduct of DDPT with Methyl Propiolate

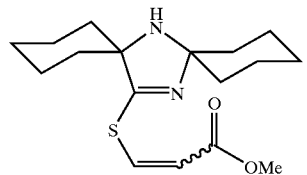

A mixture of DDPT (0.06 g, 0.252 mmol) and methyl propiolate (0.063 g, 0.75 mmol) in deuterated chloroform (CDCl$_3$, 1 mL) was heated at 45° C. for 24 h followed by standing at room temperature for 3 days. Solvent evaporation yielded the product depicted above as a light-yellow, crystalline solid (0.08 g, 99%). IR: 2932, 2854, 1716, 1603, 1448 cm$^{-1}$; $^1$H NMR (CDCl$_3$, 500 MHz): δ 8.35 (d, J=15.1 Hz, 0.4 H), 8.25 (d, J=10 Hz, 0.6 H), 6.15 (d, J=15.1 Hz, 0.4 H), 6.07 (d, J=10 Hz, 0.6 H), 3.71 (s, —CH$_3$), 3.75 (s, —CH$_3$), 3.72 (s, —CH$_3$), 1.9–1.1 (m, 20 H) ppm; $^{13}$C NMR (CDCl$_3$, 125 MHz): δ 170.9, 169.3, 166.9, 165.3, 153.0, 141.6, 141.0, 118.4, 115.1, 91.5, 91.0, 74.9, 74.3, 72.5, 72.5, 52.9, 51.6, 51.5, 36.7, 36.6, 25.4, 25.3, 25.0, 23.4, 23.3, 22.14, 22.12 ppm. The cis/trans ratio was 60/40. The product was soluble in EXCEL HC 100 at 5 weight % at 40° C.; ca. 10 weight % at 100° C. A small amount of solid precipitated after 30 minutes.

Example 15

Adduct of TMIT and an Imine Mixture

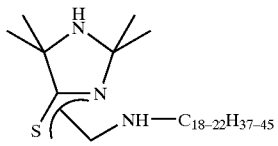

A mixture of TMIT (0.5 g, 3.16 mmol) and the formaldehyde imine (1.17 g, 3.2 mmol) of a mixture of branched C$_{18}$–C$_{22}$ tertiary alkyl primary amines (mixture of amines available from Rohm and Haas Co. under the name Primene™ JM-T Amine) was heated in a sample vial at 120° C. for 1 h and the obtained liquid was cooled to room temperature yielding a thick syrup. IR: 3302, 1672, 1481, 1465, 1377 cm$^{-1}$; $^1$H NMR (CDCl$_3$, 500 MHz): δ 5.4 (bm), 5.1 (s), 4.45–4.33 (5 s), 1.56–0.81 (3 m) ppm; $^{13}$C NMR (CDCl$_3$, 125 MHz): δ 208.4, 208.0, 206.5, 82.78, 82.42, 78.05, 70.88, 69.58, 69.42, 69.27, 68.35, 54.95, and several peaks at 40–14 ppm. The product was soluble in EXCEL HC 100 at 10 weight % at 100° C.; at room temperature, 5% of the solid precipitated overnight.

Example 16

Adduct of TMIT and an Imine Mixture

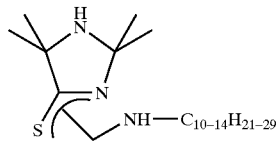

A mixture of TMIT (7.9 g, 50 mmol) and the formaldehyde imine of a mixture of branched $C_{18}$–$C_{22}$ tertiary alkyl primary amines (mixture of amines available from Rohm and Haas Co. under the name Primene™ 81-R Amine) (9.85 g, 50 mmol) were heated in a sample vial at 120–150° C. for about 2 h, and the obtained liquid was cooled to room temperature yielding a thick syrup. IR: 3305, 2959, 1687, 1481, 1465, 1378, 11756, 769 cm$^{-1}$; $^1$H NMR (CDCl$_3$, 500 MHz): δ 4.5–4.3 (bm), 1.5–1.38 (several sharp & overlapping singlets), 1.3–0.7 (bm) ppm; $^{13}$C NMR (CDCl$_3$, 125 MHz): δ 208.6, 208.0, 206.5, 82.79, 82.78, 78.04, 70.88, 69.42, 68.32, 54.42, and several peaks at 35–5 ppm.

Example 17

Adduct of a cis-trans Methyl, Ethyl TAIT Mixture and an Imine Mixture

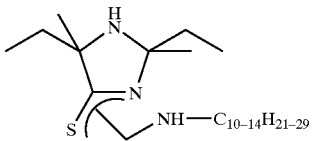

A mixture of cis-trans TAIT mixture prepared from methyl ethyl ketone (see Example 7) (0.56 g, 3 mmol) and the formaldehyde imine of a mixture of branched $C_{18}$–$C_{22}$ tertiary alkyl primary amines (mixture of amines available from Rohm and Haas Co. under the name Primene™ 81-R Amine) (0.59 g, 3 mmol) were heated in a sample vial at 110° C. for 1 h and the obtained liquid was cooled to room temperature yielding a thick syrup. IR: 3311, 3143, 2962, 1689, 1485, 1378, 1161, 787, 738 cm$^{-1}$; $^1$H NMR (CDCl$_3$, 500 MHz): δ 4.95 (m) 4.5–4.0 (m), 2.25 (bm), 1.8–0.6 (three broad multiplets) ppm; $^{13}$C NMR (CDCl$_3$, 125 MHz): δ 207.6, 207.3, 207.2, 206.2, 205.9, 85.6–85.3 (overlapping peaks), 80.9, 80.8, 73.6, 73.4, 72.1, 71.9, 67.9, 54.0, and several peaks at 36–8 ppm.

Example 18

Efficacy Testing and Performance of ZDDP Combinations

Efficacy of several oil formulations was tested, including the base oil EXCEL HC 100; one containing a commercial anti-wear ZDDP-based additive, Elco™-103 (contains a mixture of C-4 alkyl esters, formulated at 80–85% in petroleum distillates; sold by Elco Corp., Cleveland, Ohio); four formulations, each one containing one of the products of Examples 2, 15, 16 and 17; and several containing various combinations of ZDDP and the aforementioned products. The compositions, amounts, and the results of the ASTM D-4172 four-ball wear test for scar diameter in mm (see Example 9) are tabulated in Table 3.

TABLE 3

| Additive in base oil | Total amount (wt. %) | Scar diameter |
| --- | --- | --- |
| none | — | 0.92 |
| Elco ™-103 | 1 | 0.75 |
| Ex. 2 | 1 | 0.7 |
| Ex. 2: Elco ™-103, 1:1 | 1 (0.5 + 0.5) | 0.5 |
| Ex. 15 | 1 | 0.77 |
| Ex. 15: Elco ™-103, 3:1 | 1 (0.75 + 0.25) | 0.58 |
| Ex. 15: Elco ™-103, 1:1 | 1 (0.5 + 0.5) | 0.50 |
| Ex. 15: Elco ™-103, 1:3 | 1 (0.25 + 0.75) | 0.53 |
| Ex. 16 | 1 | 0.81 |
| Ex. 16: Elco ™-103, 1:1 | 1 (0.5 + 0.5) | 0.43 |
| Ex. 17 | 1 | 0.83 |
| Ex. 17: Elco ™-103, 1:1 | 1 (0.5 + 0.5) | 0.49 |

The results demonstrate that combinations of the compounds having formula (I) and a ZDDP display a synergistic improvement in anti-wear properties (i.e., smaller scar diameter) relative to either compound alone.

What is claimed is:

1. A composition comprising:

(a) from 1% to 99% of at least one compound having the formula

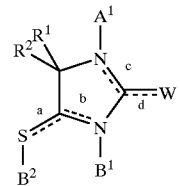

wherein W represents two groups, $R^3$ and $R^4$ bonds a and b are single or double bonds, provided that one of a and b is a single bond and the other is a double bond; c is a single bond, and d is two single bonds;

$A^1$, $B^1$ and $B^2$ are independently hydrogen, alkyl, alkenyl, aralkyl,

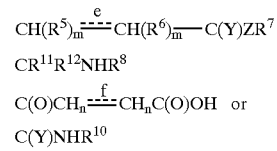

provided that $B^1$ is absent when b is a double bond, $B^2$ is absent when a is a double bond;

$R^1$, $R^2$, $R^3$ and $R^4$ are independently hydrogen, alkyl, alkenyl, aryl or aralkyl; or $R^1$ and $R^2$, or $R^3$ and $R^4$, combine with the carbon atom to which they are attached to form an alkyl or alkenyl ring; Y is O or S; Z is O, S or $NR^9$; m is 0 when bond e is a double bond and 1 when e is a single bond; n is 1 when bond f is a double bond and 2 when f is a single bond; $R^5$ is $C(Y)ZR^7$, hydrogen or $C_1$–$C_4$ alkyl; $R^6$ is hydrogen or $C_1$–$C_4$ alkyl; $R^7$, $R^8$, $R^9$, $R^{10}$, $R^{11}$ and $R^{12}$ are independently hydrogen, alkyl, alkenyl, aryl or aralkyl;

provided that at least one of $A^1$, $B^1$ and $B^2$ is present and is not hydrogen; and (b) from 1% to 99% of at least one dithiophosphate.

2. The compound of claim 1 in which $A^1$, $B^1$ and $B^2$ are independently hydrogen,

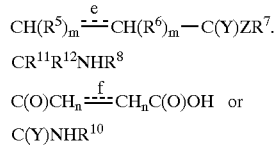

3. The composition of claim 2 in which the dithiophosphate is a ZDDP; in which the composition comprises from 20% to 80% of said at least one compound and from 20% to 80% of ZDDP; and in which Y and Z are O, e is a single bond and m is one.

4. A composition comprising:

(a) from 0.05% to 15% of a compound having the formula

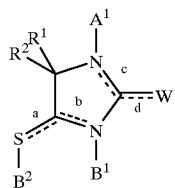

wherein W represents two groups, $R^3$ and $R^4$; bonds a and b are single or double bonds, provided that one of a and b is a single bond and the other is a double bond; c is a single bond, and d is two single bonds;

$A^1$, $B^1$ and $B^2$ are independently hydrogen, alkyl, alkenyl, aralkyl,

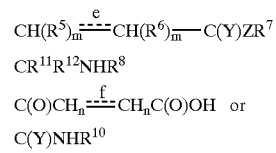

provided that $B^1$ is absent when b is a double bond, $B^2$ is absent when a is a double bond;

$R^1$, $R^2$, $R^3$ and $R^4$ are independently hydrogen, alkyl, alkenyl, aryl or aralkyl; or $R^1$ and $R^2$, or $R^3$ and $R^4$, combine with the carbon atom to which they are attached to form an alkyl or alkenyl ring; Y is O or S; Z is O, S or $NR^9$; m is 0 when bond e is a double bond and 1 when e is a single bond; n is 1 when bond f is a double bond and 2 when f is a single bond; $R^5$ is $C(Y)ZR^7$, hydrogen or $C_1$–$C_4$ alkyl; $R^6$ is hydrogen or $C_1$–$C_4$ alkyl; $R^7$, $R^8$, $R^9$, $R^{10}$, $R^{11}$ and $R^{12}$ are independently hydrogen, alkyl, alkenyl, aryl or aralkyl;

provided that at least one of $A^1$, $B^1$ and $B^2$ is present and is not hydrogen;

(b) from 0.01% to 10% at least one dithiophosphate; and (c) a lubricating oil.

5. The composition of claim 4 in which $A^1$, $B^1$ and $B^2$ are independently hydrogen,

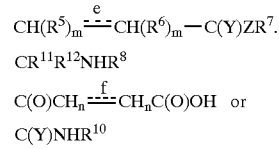

6. The composition of claim 5 in which the dithiophosphate is a ZDDP; in which the composition comprises from 0.1% to 5% of said at least one compound and from 0.1% to 5% of a ZDDP; and in which Y and Z are O, e is a single bond and m is one.

7. The composition of claim 6 comprising from 0.1% to 2% of said at least one compound and from 0.1% to 2% of a ZDDP, wherein a ratio of amounts of said at least one compound to the ZDDP is from 1:4 to 4:1.

8. A method of improving anti-wear and anti-corrosion characteristics of a lubricating oil by adding:

(a) from 0.05% to 15% of a compound having the formula

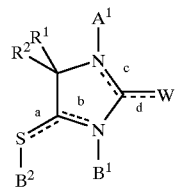

wherein W represents two groups, $R^3$ and $R^4$; bonds a and b are single or double bonds, provided that one of a and b is a single bond and the other is a double bond; c is a single bond, and d is two single bonds;

$A^1$, $B^1$ and $B^2$ are independently hydrogen, alkyl, alkenyl, aralkyl,

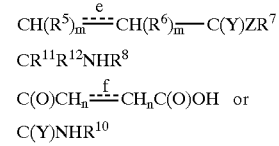

provided that $B^1$ is absent when b is a double bond, $B^2$ is absent when a is a double bond;

$R^1$, $R^2$, $R^3$ and $R^4$ are independently hydrogen, alkyl, alkenyl, aryl or aralkyl; or $R^1$ and $R^2$, or $R^3$ and $R^4$, combine with the carbon atom to which they are attached to form an alkyl or alkenyl ring; Y is O or S; Z is O, S or $NR^9$; m is 0 when bond e is a double bond and 1 when e is a single bond; n is 1 when bond f is a double bond and 2 when f is a single bond; $R^5$ is $C(Y)ZR^7$, hydrogen or $C_1$–$C_4$ alkyl; $R^6$ is hydrogen or $C_1$–$C_4$ alkyl; $R^7$, $R^8$, $R^9$, $R^{10}$, $R^{11}$ and $R^{12}$ are independently hydrogen, alkyl, alkenyl, aryl or aralkyl;

provided that at least one of $A^1$, $B^1$ and $B^2$ is present and is not hydrogen; and (b) from 0.01% to 10% of at least one dithiophosphate.

9. The method of claim 8 in which $A^1$, $B^1$ and $B^2$ are independently hydrogen,

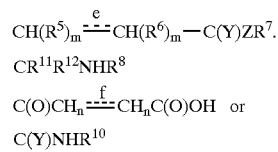

10. The method of claim 9 in which the dithiophosphate is a ZDDP; in which from 0.1% to 5% of said at least one compound and from 0.1% to 5% of a ZDDP are added; and in which Y and Z are O, e is a single bond and m is one.

11. The compound of claim 3 in which $A^1$, $B^1$ and $B^2$ are independently hydrogen or $CHR^5CHR^6C(O)OR^7$, wherein $R^5$ and $R^6$ are hydrogen or $C_1$–$C_4$ alkyl.

12. The compound of claim 11 in which $A^1$ is hydrogen, and $B^1$ and $B^2$ are independently hydrogen or $CH_2CH_2C(O)O$-alkyl.

13. The compound of claim 7 in which $A^1$, $B^1$ and $B^2$ are independently hydrogen or $CHR^5CHR^6C(O)OR^7$, wherein $R^5$ and $R^6$ are hydrogen or $C_1$–$C_4$ alkyl.

14. The compound of claim 13 in which $A^1$ is hydrogen, and $B^1$ and $B^2$ are independently hydrogen or $CH_2CH_2C(O)O$-alkyl.

15. The compound of claim 10 in which $A^1$, $B^1$ and $B^2$ are independently hydrogen or $CHR^5CHR^6C(O)OR^7$, wherein $R^5$ and $R^6$ are hydrogen or $C_1$–$C_4$ alkyl.

16. The compound of claim 15 in which $A^1$ is hydrogen, and $B^1$ and $B^2$ are independently hydrogen or $CH_2CH_2C(O)O$-alkyl.

* * * * *